United States Patent [19]

Adolph

[11] 4,001,291

[45] Jan. 4, 1977

[54] 2,2,2-FLUORODINITROETHANETHIOL AND METHOD OF PREPARATION

[75] Inventor: Horst G. Adolph, Beltsville, Md.

[73] Assignee: The United States of America as represented by the Secretary of the Navy, Washington, D.C.

[22] Filed: Mar. 11, 1976

[21] Appl. No.: 666,103

[52] U.S. Cl. .......................... 260/455 R; 149/88; 260/609 R; 260/644

[51] Int. Cl.² .............. C07C 153/09; C07C 149/16; C07C 149/20; C06B 25/00

[58] Field of Search ...... 149/88; 260/455 R, 609 R, 260/644

[56] References Cited

UNITED STATES PATENTS

| | | | |
|---|---|---|---|
| 2,259,869 | 10/1941 | Allen | 260/455 R |
| 2,894,991 | 7/1959 | Barr et al. | 260/609 R |
| 2,961,470 | 11/1960 | Sheppard | 260/609 R |
| 3,223,725 | 12/1965 | Hill | 149/88 |
| 3,274,259 | 9/1966 | Hartman | 260/609 R |
| 3,316,292 | 4/1967 | Schaeffler | 260/644 |
| 3,387,044 | 6/1968 | Grakauskas et al. | 149/88 |
| 3,522,313 | 7/1970 | Reece et al. | 260/609 R |
| 3,624,129 | 11/1971 | Kamley | 149/88 |
| 3,823,191 | 7/1974 | Dighe | 260/609 R |
| 3,966,825 | 6/1976 | Marx | 260/609 R |

OTHER PUBLICATIONS

Beard, C. D., et al., J. Org. Chem., vol. 38, No. 21, pp. 3673–3677 (1973).

Primary Examiner—Benjamin R. Padgett
Assistant Examiner—T. S. Gron
Attorney, Agent, or Firm—R. S. Sciascia; A. L. Branning; R. D. Johnson

[57] ABSTRACT

Novel thiols of the formula

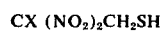

wherein X is nitro, fluoro, chloro, bromo, or lower alkyl of from 1 to 4 carbon atoms, are prepared by contacting triflates of the formula

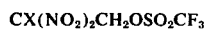

with

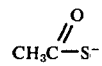

to form thioacetals of the formula

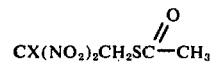

which are then isolated from the reaction mixture and subjected to acid hydrolysis to form the thiols. The energy content of unsaturated propellant and explosive binders can be increased by the free radical addition of the nitro and halonitro thiols of this invention to the binders.

15 Claims, No Drawings

2,2,2-FLUORODINITROETHANETHIOL AND METHOD OF PREPARATION

BACKGROUND OF THE INVENTION

This invention relates to thiols and more particularly to nitro and halonitro thiols.

Unsaturated polymers such as polybutadienes and polyurethanes derived from dihydroxy terminated polybutadiene prepolymers are frequently used as explosive and propellant binders. It is known in the art that the energy content of these polymers may be increased by attaching nitro groups onto them. See for example Propellants Manufacture, Hazards, and Testing (No. 88 in the Advances in Chemistry Series, American Chemical Society, Washington, D.C., 1969), page 79. It would be desirable, therefore, to provide effective means of adding nitro groups to these polymeric binders.

SUMMARY OF THE INVENTION

Accordingly, one object of this invention is to provide novel chemical compounds.

Another object of this invention is to form novel chemical compounds containing nitro groups.

A further object of this invention is to provide novel chemical compounds which can easily be added to unsaturated polymeric binders to form stable products.

Still another object of this invention is to provide a novel method of synthesizing chemical compounds.

These and other objects of this invention are accomplished by providing compounds of the formula $$CX(NO_2)_2CH_2SH$$

wherein X is selected from the group consisting of nitro, fluoro, chloro, bromo, or lower alkyl of from 1 to 4 carbon atoms. These thiols are prepared by contacting a triflate of the formula $$CX(NO_2)_2CH_2OSO_2CF_3$$

with a thioacetate ion of the formula

to form a thioacetate of the formula

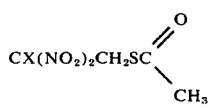

which is separated from the reaction mixture and then acid hydrolyzed to form the thiol of the formula $$CX(NO_2)_2CH_2SH.$$

These novel thiols may be added to polymeric binders containing carbon-carbon double bonds by normal state of the art free radical addition processes. In this manner the energy content of the binders can be increased, making them more suitable as explosive or propellant binders.

DETAILED DESCRIPTION OF THE PREFERRED EMBODIMENT

The reaction sequence for preparing the novel nitro and halonitro thioacetates and thiols of the present invention may be depicted as follows:

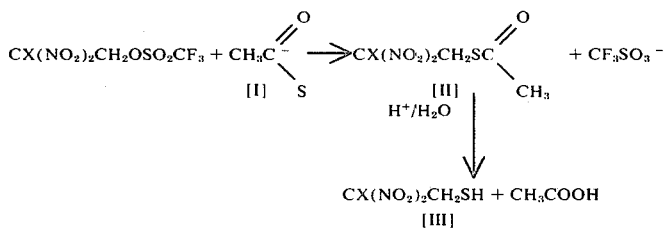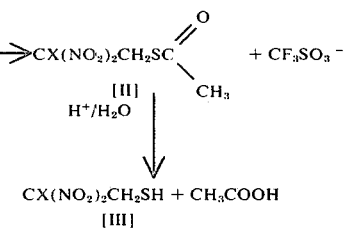

wherein X is nitro, fluoro, chloro, bromo, or lower alkyl of from 1 to 4 carbon atoms.

The substituent X in the thioacetates [II] and thiols [III] may be selected to maximize certain properties in these compounds. For instance, the explosive energy of a compound is greatest when X is nitro. Thus, for maximum energy, $C(NO_2)_3CH_2SCOCH_3$ is the preferred thioacetate and $C(NO_3)_3CH_2SH$ is the preferred thiol. On the other hand, for greatest thermal stability, X is preferably fluoro, chloro, or bromo, more preferably fluoro or chloro, and most preferably fluoro. In this case, the preferred thioacetates are $CF(NO_2)_2CH_2SCOCH_3$, $CCl(NO_2)_2CH_2SCOCH_3$, and $CBr(NO_2)_2CH_2SCOCH_3$, with $CF(NO_2)_2CH_2SCOCH_3$ and $CCl(NO_2)_2CH_2SCOCH_3$ being more preferred, and with $CF(NO_2)_2CH_2SCOCH_3$ being the most preferred thioacetate. Similarly, the preferred thiols are $CF(NO_2)_2CH_2SH$, $CCl(NO_2)_2CH_2SH$, and $CBr(NO_2)_2CH_2SH$, with $CF(NO_2)_2CH_2SH$ and $CCl(NO_2)_2CH_2SH$ being more preferred, and with $CF(NO_2)_2CH_2SH$ being the most preferred thiol. Finally, X may be lower alkyl of from 1 to 4 carbon atoms with methyl being the preferred alkyl group.

The nitroethyl and halonitroethyl thioacetate compounds [II] are prepared by reacting nitroethyl or halonitroethyl triflate compounds [I] with the thioacetate ion,

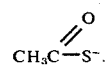

The thioacetate ion may be added in the form of a water-soluble metal salt of thioacetic acid (e.g. potassium thioacetate).

The nitroethyl and halonitroethyl triflates can be prepared from the corresponding nitroethyl and halonitroethyl alcohols by the method disclosed by Charles D. Beard, Kurt Baum, and Vytautas Grakauskas in "Synthesis of Some Novel Trifluoromethanesulfonates and Their Reaction With Alcohols", 38 J. Org. Chem. 3673 at 3675 (1973). This synthesis uses equimolar amounts of alcohol, pyridine, and trifluoromethanesulfonic anhydride to produce the triflate. The following alcohols $CF(NO_2)_2CH_2OH$, $CCl(NO_2)_2CH_2OH$, $CBr(NO_2)_2CH_2OH$, $C(NO_2)_3CH_2OH$, and $RC(NO_2)_2CH_2OH$ (wherein R = lower alkyl of from 1 to 4 carbon atoms) may be used to produce the following triflates:

$CF(NO_2)_2CH_2OSO_2CF_3$, $CCl(NO_2)_2CH_2OSO_2CF_3$, $CBr(NO_2)_2CH_2OSO_2CF_3$, $C(NO_2)_3CH_2OSO_2CF_3$, and $RC(NO_2)_2CH_2OSO_2CF_3$, respectively.

At elevated temperatures, the nitroalkyl and halonitroalkyl triflates [I] and thioacetates [II] may be unstable in neutral or slightly basic solutions. As a result, if the mixture is heated, the yield of thioacetate [II] may be reduced by side reactions and decomposition. Therefore, the synthesis of the thioacetates [II] is preferably carried out at room temperature. The mixture should also be cooled and stirred to prevent overheating when the reactants are first brought together.

After the thioacetate product, $$CX(NO_2)_2CH_2SC\overset{\displaystyle O}{\underset{}{\parallel}}CH_3,$$

has been isolated from the mixture, it is converted by standard acid hydrolysis (e.g. 75% $H_2SO_4$ at 60° C) into the thiol [III], $CX(NO_2)_2CH_2SH$. Because the above mentioned side reactions do not occur in acidic solutions, this hydrolysis step may be performed at elevated temperatures.

Polymers containing olefinic groups (e.g. polydienes such as polybutadiene, and polyurethanes made from hydroxy-terminated polybutadiene polymers) are often used as binders in explosives and propellants. The thiols of the present invention provide a convenient means by which energetic nitro and halonitro groups may be grafted on to these olefinic polymer binders by free radical addition. This is based on the fact that thiols readily enter into free radical addition reactions with olefins to produce stable products. See for example Organic Reactions, Volume 13 (John Wiley and Sons, Inc, New York, 1963), pp. 165–190. In this manner, the energy content of these polymers may be increased.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE I

Preparation of 2,2,2-fluorodinitroethyl thioacetate

To a mixture of 30.5g crude 2,2,2-fluorodinitroethyl triflate and 100 ml of 75% aq. acetonitrile was added with stirring and cooling 12.5 g potassium thioacetate. The mixture was stirred for 2–3 days at room temperature, poured over crushed ice, the product extracted into methylene chloride, and the extract dried and distilled. Obtained was 15.1 g fluorodinitroethyl thioacetate of about 90% purity.

NMR ($CDCl_3$): $\delta 2.41$ singlet; $\delta 4.26$ doublet ($J_{HF}$ 16 CPS); the area ratio of the signal near 2.41 to the signal near 4.26 is about 2:3.

IR (film): 1730 cm$^{-1}$ (C = O); 1605 and 1310 cm$^{-1}$ ($NO_2$ stretch); 1210, 1130, 1055, 965, 850, and 805 cm$^{-1}$.

EXAMPLE II

Preparation of 2,2,2-fluorodinitrothiol 3.6 g of this product was heated with 36 ml 75% sulfuric acid at about 60° C for 24 hrs with efficient stirring. After pouring the product over ice, the mixture was extracted 3 times with methylene chloride, the extracts were dried ($MgSO_4$) and freed from solvent in vacuo. Obtained was 2.7 g (93.5%) crude fluorodinitroethanethiol of about 90% purity.

NMR ($CDCl_3$): $\delta 1.92$ t ($J_{HH}$9 cps) —SH; $\delta 3.73$ double d ($J_{HH}$17cps; $J_{HH}$9 cps) —$CH_2$; the area ratio of the signal near 1.92 to the signal near 3.73 is about 1:2.

IR (film): —SH at about 2600 cm$^{-1}$, nitro bands near 1600 and 1300 cm$^{-1}$, C—S probably at 825 cm$^{-1}$.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the U.S. is:

1. A compound of the formula $$CX(NO_2)_2CH_2SC\overset{\displaystyle O}{\underset{\displaystyle CH_3}{\diagdown\!\!\!\!\diagup}}$$

wherein X is selected from the group consisting of nitro, fluoro, chloro, bromo, and lower alkyl of from 1 to 4 carbon atoms.

2. The compound of claim 1 wherein X is selected from the group consisting of fluoro, chloro, and bromo.

3. The compound of claim 2 wherein X is selected from the group consisting of fluoro and chloro.

4. The compound of claim 3 wherein X is fluoro.

5. The compound of claim 1 wherein X is a lower alkyl of from 1 to 4 carbon atoms.

6. The compound of claim 5 wherein X is methyl.

7. The compound of claim 1 wherein X is nitro.

8. A compound of the formula $CX(NO_2)_2CH_2SH$ wherein X is selected from the group consisting of nitro, fluoro, chloro, bromo, and lower alkyl of from 1 to 4 carbon atoms.

9. The compound of claim 8 wherein X is selected from the group consisting of fluoro, chloro, and bromo.

10. The compound of claim 9 wherein X is selected from the group consisting of fluoro and chloro.

11. The compound of claim 10 wherein X is fluoro.

12. The compound of claim 8 wherein X is a lower alkyl of from 1 to 4 carbon atoms.

13. The compound of claim 12 wherein X is methyl.

14. The compound of claim 8 wherein X is nitro.

15. A process for making nitro and halonitro thiols comprising:

a. contacting a triflate of the formula $$CX(NO_2)_2CH_2OSO_2CF_3$$

with

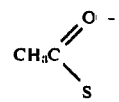

to produce a thioacetate of the formula $$CX(NO_2)_2CH_2SC-CH_3;$$

b. isolating the thioacetate from the reaction mixture; and then c. subjecting the thioacetate to normal acid hydrolysis to produce a thiol of the formula $$CX(NO_2)_2CH_2SH,$$

wherein X is selected from the group consisting of nitro, fluoro, chloro, bromo, or lower alkyl of from 1 to 4 carbon atoms.

* * * * *